United States Patent [19]

Huffman et al.

[11] Patent Number: 4,469,680

[45] Date of Patent: Sep. 4, 1984

[54] IODINATED VASOPRESSIN ANTAGONISTS

[75] Inventors: William F. Huffman, Malvern; Michael L. Moore, Media, both of Pa.

[73] Assignee: SmithKline Beckman Corporation, Philadelphia, Pa.

[21] Appl. No.: 511,120

[22] Filed: Jul. 6, 1983

[51] Int. Cl.$^3$ .................... A61K 37/00; A61K 43/00; G01N 33/00; C07C 103/52
[52] U.S. Cl. .................... 424/177; 424/1.1; 260/112.5 R
[58] Field of Search .................. 424/177; 260/112.5 R

[56] References Cited

U.S. PATENT DOCUMENTS 4,367,225  1/1983  Manning et al. .................... 424/177

OTHER PUBLICATIONS

G. Flouret et al., Biochemistry 16 2119 (1977).

Primary Examiner—Delbert R. Phillips
Attorney, Agent, or Firm—William H. Edgerton; Richard D. Foggio; Alan D. Lourie

[57] ABSTRACT

A series of vasopressin antagonists which have a 3'-iodo-tyrosine unit at position 2 are prepared by iodination of the tyrosine congeners. The compounds have antagonist activity manifested by an aquaretic effect and, also, are useful in studying various biological reactions.

8 Claims, No Drawings

IODINATED VASOPRESSIN ANTAGONISTS

This invention relates to iodine-containing cyclic peptides which are vasopressin antagonists. More specifically, the structures of these new cyclic peptides have 1-(β-mercapto-β,β-cyclopentamethylenepropionic acid (Pmp) and five amino acid units cyclized into a 6-unit ring by means of a sulfur derived from a cysteine unit and a sulfur from the Pmp unit, the ring further being distinguished by having an iodinated tyrosyl member at position 2. The cyclic structures of the compounds have either a known dipeptide or a known tripeptide tail attached via an amido linkage to the cysteine unit of the ring.

BACKGROUND OF THE INVENTION

M Manning, W. H. Sawyer and coworkers have published a series of papers describing various [1-(β-mercapto-β,β-cyclopentamethylenepropionic acid), 4-valine]-arginine-vasopressin congeners which have anti-vasopressin activity. Among these are J. Med. Chem. 25 414–419 (1982), J. Med. Chem. 25 45–50 (1982), EPA No. 61,356 and U.S. Pat. No. 4,367,225. Certain 2-D-tyrosyl and 2-L-tyrosyl containing starting materials for the compounds of this present invention are disclosed in these publications.

None of these publications describe any vasopressin-like structures which have an iodine containing unit in the polypeptide ring.

In the description herein and in the claims, the nomenclature common in the art of peptide and vasopressin chemistry is used. When no configuration is noted, the amino acid unit is in the L, or naturally occuring, form.

DESCRIPTION OF THE INVENTION

The compounds of the invention are illustrated by the following structural formula:

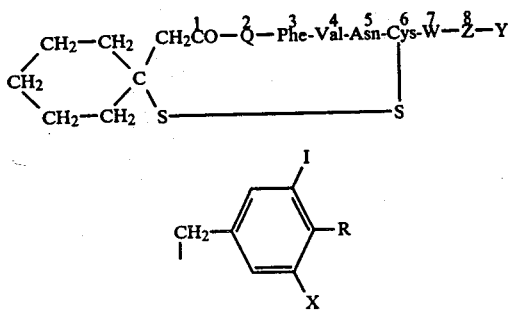

in which:
Q is D- or L-NH—CH—CO—;
Y is NH₂, OH, Gly or Gly(NH₂);
W is Pro;
Z is D- or L-Arg;
X is H or when R is —OH, I and
R is OH or O-alk of 1-2 carbons; or a pharmaceutically acceptable salt or prodrug derivative thereof.

"Alk" represents a lower alkyl of 1-2 carbons which are optionally attached to the oxygen substituent of the tyrosine unit at position 2. Such alkyl substituents include methyl or ethyl. When the term, "vasopressin", is used, it means L-arginine vasopressin (AVP) unless otherwise modified. The AVP derivatives of this invention are preferred.

A subgeneric group of compounds of this invention comprises compounds of formula I in which X is H and R is —OH.

Individual compounds of interest are [1-(β-mercapto-β,β-cyclopentamethylenepropionic acid)-2-D-(3'-iodo)-tyrosine-4-valine-8-arginine-9-desglycine]-vasopressin or [1-(β-mercapto-β,β-cyclopentamethylenepropionic acid)-2-D-(3'-iodo)-tyrosine-4-valine-8-arginine]-vasopressin. While these are the complete names of representative compounds of this invention, it is convenient to use abbreviations known in the vasopressin art with a superscript numeral to indicate position in the cyclic polypeptide and parenthetical designation for substituents or acyl and ether derivatives of the standard amino acid units.

Also included in this invention are addition salts, prodrugs and complexes of the described compounds, especially the nontoxic, pharmaceutically acceptable salts. The acid addition salts are prepared in standard manner in a suitable solvent from the parent compound and an excess of an acid, such as hydrochloric, hydrobromic, sulfuric, phosphoric, acetic, maleic, succinic, ethanedisulfonic or methanesulfonic acids. Normally, the compounds of formula I in which Y is OH are used in the non-salt form. Prodrugs are usually simple ester derivatives such as the $C_{2-6}$-alkyl esters which are degraded in vivo to give the active vasopressin antagonist.

The iodinated cyclic peptides of this invention are prepared by reaction of the vasopressin peptides having D or L-tyrosine at the 2-position with about one mole equivalent of iodonium ion (I⊕) or iodine monochloride to prepare the preferred monoiodo compounds. The reaction is run at room temperature in any solvent in which the reactants are soluble. Aqueous buffer solutions are very useful. The iodonium reagent is also conveniently prepared in situ as is commonly used in the art, for example, using an alkali metal iodide plus an oxidizing agent. When the tyrosyl unit is in the ether form, forcing conditions are used to form the iodo compound.

The intermediates for the iodination reaction are prepared by cyclizing a linear octa- or nonapeptide by means of the two mercapto groups, respectively at the cysteine unit (Cys) at position 6 and the β-mercapto-β,β-cyclopentamethylenepropionic acid unit (Pmp) at position 1. The cyclization reaction occurs in the presence of any mild oxidizing agent capable of oxidizing a mercaptan to a disulfide.

For example, oxidation of the following linear peptide;

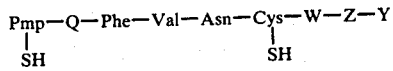

in which W, Z and Y are as defined for formula I and Q is the desiodo tyrosyl unit, with the mercapto groups being members of the Pmp and Cys units, is carried under mild oxidation conditions. An excess of an alkali metal ferricyanide, such as potassium or sodium ferricyanide, is used with the linear intermediate dissolved in a suitable unreactive solvent, preferably in an aqueous solvent, at a neutral pH, about 7-7.5, at ambient temperature or lower until the reaction is substantially complete. Preferably, the concentrations of the linear peptide dimercaptan and the oxidizing agent are low, say 0.1 molar concentration of oxidizing agent in several liters of aqueous solution to cyclize 1-5 grams of dimercaptan.

The linear intermediates are conveniently prepared using solid-phase methods of peptide synthesis as discussed in M. Manning et al., J. Med. Chem. 25 46 (1982). A commercial benzhydrylamine support resin (BHR) is used to prepare the end products of formula I in which Y is $NH_2$ or glycinamide and a chloromethyl support resin (CMR) is used to prepare the compounds of formula I in which Y is OH or glycine.

The peptide chain of the linear peptides of formula II is built up, stepwise, proceeding from unit 8 or 9 working toward unit 1. Each unit is properly protected as known in the peptide art and as described below. The sequence of step reactions is conveniently carried out in a Beckman 990B peptide synthesizer without isolation of each intermediate peptide. The details of the procedure are in U.S. Pat. No. 4,367,225.

The compounds of this invention have vasopressin antagonist activity. Vasopressin is known to contribute to the anti-diuretic mechanism of action within the kidney. When the action of these compounds antagonizes that of the natural anti-diuretic hormone (ADH), the body excretes water due to an increased permeability of the terminal portions of the renal tubule. We believe the mechanism of action is at the vasopressin receptors ($V_2$-receptors) located on the plasma membrane of certain renal epithelial cells. The most notable pharmocodynamic effect of the ADH antagonists of the invention is that of a water diuretic rather than of a natriuretic such as a thiazide.

Any patient suffering from the syndrome of inappropriate antidiuretic hormone secretion (SIADH) or from an undesirable edematous condition is a target for the claimed compounds. Examples of clinical conditions indicated for the compounds of this invention include hypertension, hepatic cirrhosis, congestive heart failure or a component of any traumatic condition resulting from serious injury or disease.

The second group of vasopressin receptor sites are the vascular pressor sites ($V_1$-receptors) within the cardiovascular system itself. These may also be somewhat antagonized by the compounds of this invention.

The compounds of this invention, therefore, are used to treat edema or to expell water in patients in need of such treatment by administering parenterally or by insufflation a nontoxic but effective quantity of the chosen compound, preferably combined with a pharmaceutical carrier. Dosage units of the active ingredient are selected from the range 0.01 to 10 mg/kg, preferably 0.05 to 5 mg/kg, based on a 70 kg patient. The dosage units are applied from 1 to 5 times daily.

The pharmaceutical composition which contains an active ingredient of formula I comprises a dosage unit as described above dissolved or suspended in a standard liquid carrier, such as isotonic saline, contained in an ampoule or a multiple dose vial suitable for a parenteral injection such as for intravenous, subcutaneous or intramuscular administration. A composition for insufflation may be similar but is usually administered in a metered dose applicator or inhaler. Pulverized powder compositions may, also, be used along with oily preparations, gels, buffers for isotonic preparations, emulsions or aerosols.

The compounds of this invention have been demonstrated to have antagonistic activity toward the natural antidiuretic hormone (anti-ADH activity), in vitro, in the medullary tissue of hog kidney and, in vivo, in the hydropenic rat.

HOG KIDNEY ASSAY

A. Preparation of renal medullary membranes:

The medullary tissue of 24 kidneys of freshly slaughtered hogs is carefully dissected. The tissue is homogenized at 0° in a blender at maximal speed for one minute in 5 mM tris(hydroxymethyl)aminomethane (TRIS) buffer pH 8.0 containing 3.0 mM magnesium chloride, 1.0 mM ethylenediaminetetraacetic acid and 0.25M sucrose (TRIS-sucrose buffer used at 10 ml of buffer per gram of tissue.) The tissue is homogenized in a Potter-Elvehjem homogenizer equipped with a Teflon pestle. The homogenate is passed through one layer of cheesecloth with one volume of TRIS-sucrose buffer. The 300 times gravity supernatant is centrifuged at 1200 times gravity. The resulting pellet is washed with 5 mM TRIS buffer at pH 8 containing 3.0 mM magnesium chloride and 1 mM ethylenediaminetetracarboxylic acid (hypotonic Tris buffer; $6 \times 10$ ml of buffer per gram of tissue). The washed pellet is suspended in hypotonic TRIS buffer (1.0 ml per gram of tissue) and stored in aliquots in liquid nitrogen.

B. Assay of Adenylate Cyclase Activity:

The incubation mixture contains 100 mM TRIS, 0.1% bovine serum albumin (BSA), 10 mM magnesium chloride, 1 mM c-adenosine monophosphate, 0.25 mM adenosine triphosphate, 0.6–1.2 uCi [$\alpha$-$^{32}P$]-adenosine triphosphate (specific activity in 30 Ci/mmol), 20 mM creatine phosphate, 1 mg creatine kinase/ml, 1 mM ethyleneglycol-bis-($\beta$-aminoethylether)-N,N'-tetraacetic acid, renal medullary membranes (0.5–1.0 mg/ml), vasopressin and the test compound. The total volume is 300 $\mu$l; the pH is 8.0 at 30°. The mixture is incubated for 20 minutes at 30°, the tubes are transferred to ice water, 100 $\mu$l of a stopping solution (1% sodium lauryl sulfate containing 10 mM cyclic-adenosine monophosphate, $^3H$ cyclic-adenosine monophosphate 1500 dpm/100 $\mu$l and 45 mM ATP; the pH was adjusted to 8.0 at 25° with 2M TRIS) is added followed by 500 ul of ice cold water. The $^{32}P$/cAMP formed was isolated by chromatography on aluminum oxide and "Dowex" AG 50W-X8. $^3H$ cAMP serves as control.

C. Test Procedure for Assay of Adenylate Cyclase Activity:

In each experiment the amount of $^{32}P$/cAMP formed in the absence of medullary membrane is determined (blank). The blank value is substracted from all experimental data. The compound is tested for its effect on basal adenylate cyclase activity and/or on vasopressin stimulated activity. Each determination is carried out in triplicate. The Ka value is derived from a Lineweaver-Burke plot. Rel. $V_{max}=(V_{max}drug/V_{max}$ vasopressin$)\times 100$. $K_i=I/[(Ka'/Ka)-1]$ where I is the concentration of the antagonist, and Ka' and Ka are the concentrations of vasopressin required to give half-maximal activity of adenylate cyclase in the presence and absence of antagonist, respectively.

D. Inhibition of Vasopressin Binding:

The incubation mixture contains 100 mM Tris, 0.5% BSA, 10 mM magnesium chloride, 1 mM cAMP, 0.25 mM ATP, $^3H$-vasopressin, test compound and membranes (0.5–1.0 mg protein/ml). The total volume is 100 $\mu$l; the pH is 8.0 at 30°. After incubating for 20 minutes at 30°, 2 ml of ice-cold 100 mM Tris:HCl buffer pH 8.1 (at 5°) containing 1.0 mM magnesium chloride, 1 mM cAMP, and 0.25 mM ATP are added and the mixture is immediately filtered through prewashed Millipore filters (the filters are prewashed with 5 ml of ice-cold 10 mM Tris:HCl buffer pH 8.1 at 5°—containing 0.1% BSA and 1 mM MgCl$_2$—Solution A). The filters are rapidly washed with 4×5 ml ice-cold solution A.

E. Test Procedure for Binding Assay:

In each experiment, the amount of $^3$H-vasopressin bound in the absence and in the presence of an excess of vasopressin (7.5×10$^{-6}$M) is measured in triplicate. These values represent total and non-specific binding, respectively. The $K_B$ of a compound is derived from the equation for competitive inhibition: $K_B = IC_{50}/(1+L/K_D)$, where IC$_{50}$ is the concentration required for 50% inhibition of $^3$H-vasopressin binding, L is the concentration of the ligand, and $K_D$ is the dissociation constant of $^3$H-vasopressin ($K_D = 3.6 \times 10^{-9}$M; 1SD=0.4×10$^{-9}$M). This is the average $K_D$ value determined on 3 preparations of hog kidney membranes.

HYDROPENIC RAT SCREEN

A. Food and water are removed from male rats approximately 18 hours prior to testing. Animals are housed 4 per metabolism cage. At 0 hour, the test compound is administered intraperitoneally to the test group and an equivalent volume of vehicle is administered to both control groups (fasted and non-fasted). Urine volume and osmolality are measured every hour for 4 hours. Test values are recorded as ml of urine excreted (cumulative), mEq/rat electrolyte excreted, mg/rat urea excreted, and osmolality in milli-Osmoles/kg H$_2$O. A tolerance test is used to determine significance. ED$_{300}$ is defined as the dose of compound (μg/kg) required to lower urine osmolality to 300 m-Osmoles/kg. ED$_{500}$ is defined as the dose of compound (μg/kg) required to lower urine osmolality to 500 m-Osmoles/kg.

TABLE I

| Compound | anti-ADH activity | | |
|---|---|---|---|
| | in vivo (Rat) ED$_{300}$ (μg/kg)* | in vitro Ki (nm) | (Pig) K$_B$ (μM) |
| A. [Pmp$^1$, D-Tyr$^2$, Val$^4$]AVP | 31.8 ± 5.4 | 30 | 0.10 |
| B. [Pmp$^1$, D-Tyr(I)$^2$, Val$^4$]AVP | 92.6 | 40 | 0.12 |
| C. [Pmp$^1$, D-Tyr(I$_2$)$^2$, Val$^4$]AVP | — | 900 | 2.4 |

*Estimated dose of peptide delivered ip-stat (μg/kg) which results in a reduction of U$_{osm}$ from hydropenic levels to 300 m-Osmoles/kg H$_2$O.

The table of biological test results presented above demonstrates that Compound B is about equivalent in activity to the prior art desiodo compound (A). The diiodo, Compound C, is substantially less active than Compound B.

The compounds of formula I whose structures have an isotopic iodo (I$^{125}$) present at position 2, also a part of this invention, are of utility in studying the pharmacokinetic behavior of the compounds in the body. They are also useful for investigating biochemical processes and mechanisms of action in vivo which involve vasopressin, its agonists or antagonists.

The following examples are intended solely to teach the preparation of the compounds of this invention. All temperatures are in degrees Centigrade.

EXAMPLE 1

[Pmp$^1$, D-Tyr$^2$, Val$^4$]-AVP (18.4 mg, 16.6 μmol, Manning et al., U.S. Pat. No. 4,367,225) was dissolved in 3 ml of potassium phosphate buffer (0.1M, pH 7.4) with gentle warming. To this was added 2 ml of a solution made up of 139 mg of sodium iodide in 100 ml of buffer (18.6 μmol) followed by 2 ml of a freshly prepared solution of 65 mg of chloramine T in 25 ml of buffer (18.5 μmol) with stirring. Reaction was allowed to continue for 1 hour at room temperature. The reaction mixture was then clarified with a few drops of glacial acetic acid and lyophilized. The lyophilizate was dissolved in 10 ml of 1% acetic acid, filtered through a 0.45μ filter and purified by preparative high pressure liquid chromatography (HPLC) (9.0 mm×25 cm Altex Ultrasphere ODS) using the solvent system 40% acetonitrile/60% water/0.25% trifluoroacetic acid. The product bearing fractions (HPLC) were pooled and evaporated to dryness. The residue was redissolved in 1% acetic acid and lyophilized to give 7.0 mg of a fluffy powder [Pmp', D-Tyr(I)$^2$, Val$^4$]-AVP which was homogeneous by HPLC and thin layer chromatography (TLC); FAB mass spectrum m/z 1234 (M+H).

EXAMPLE 2

The diiodo-D-Tyr$^2$ analog was prepared in the same preparation as the mono-iodo compound in Example 1 and was isolated as a later eluting component from the HPLC. The appropriate fractions were worked up as in Example 1 to yield 3.8 mg of fluffy white powder, homogeneous by tlc and HPLC; FAB mass spectrum m/z 1360 (M+H).

When exactly 1 mole-equivalents of iodide and chloramine T are used, the yield of mono-iodo is optimized (65% based on HPLC, not isolated).

EXAMPLE 3

For the solid-phase synthesis of Pmp(Bzl)-D-Tyr-(Br-Z)-Phe-Val-Asn-Cys(OMe-Bzl)-Pro-Arg(Tos)-Resin, Boc-Arg(Tos)-Resin (3 mM/5.4 grams of resin) was used as starting material. The appropriately protected amino acids were coupled sequentially onto the Boc-Arg(Tos)-resin, prepared by reacting Boc-Arg(Tos) as the cesium salt with commercial Merrifield resin (Cl-CH$_2$-resin) as known to the art, by using a manual program as described in the following steps:

1. washed with methylene chloride (3 times, 1 minute).
2. prewashed with 33% trifluoroacetic acid in methylene-chloride with 1% indole (1 time, 1 minute).
3. deprotection with 33% trifluoroacetic acid in methylene-chloride with 1% indole (20 minutes).
4. washed with methylene chloride (1 time, 1 minute).
5. washed with ethanol (1 time, 1 minute).
6. washed with methylene chloride (2 times, 1 minute).
7. prewashed with 10% triethylamine in methylene chloride (1 time, 1 minute).
8. neutralization with 10% triethylamine in methylene chloride (10 minutes).
9. Protected amino acid (10 mM) in triethylamine in methylene chloride and 0.5M N,N'-dicyclohexylcarbodiimide in methylene chloride (20 ml) were added and the reaction time was up to two hours.

In the case of the coupling of the Asn moiety, 1-hydroxybenzotriazole (HBT, 10 mM) was added with Boc-Asn in dry dimethylformamide. Dry dimethylformamide (DMF) was also used as solvent when Pmp(Bzl) was coupled onto the peptide resin, using 4-dimethylaminopyridine (10 mM). Completion of each coupling reaction was monitored by the ninhydrin test.

The p-methoxybenzyl group was used to protect the thiol group of Cys and the 2-bromo-carbobenzoxy group was employed to block the phenolic hydroxyl of D-Tyr.

The resulting protected Pmp(Bzl)-D-Tyr(Br-Z)-Phe-Val-Asn-Cys(OMe-Bzl)-Pro-Arg(Tos)-resin was washed well with 33% trifluoroacetic acid in methylene chloride, methylene chloride and methanol, respectively. After drying in vacuo overnight, 8.4 grams of the titled protected resin intermediate was collected.

Pmp(Bzl)-D-Tyr-(p-bromocarbobenzoxy)-Phe-Val-Asn-Cys(OMe-Bzl)-Pro-Arg(Tos)-Resin (4 g, ca. 1.5 mM) was subjected to ammonolysis using saturated ammonia/methanol solution (200 ml) in dry dimethylformamide (50 ml) at room temperature for 48 hours. After evaporation to dryness, the residue was precipitated by ethyl acetate/n-hexane and filtered to give the protected octapeptide amide (1.54 g).

This crude peptide was dissolved in liquid ammonia (250 ml) and treated with sodium/liquid ammonia solution to give Pmp-D-Tyr-Phe-Val-Asn-Cys-Pro-Arg-NH$_2$ which was, then, oxidized using 0.01M potassium ferricyanide solution in 4 l. of aqueous solution at pH 7–7.5. After the completion of oxidation reaction, the pH of aqueous solution was adjusted to pH 4.5 by adding glacial acetic acid. This solution was passed through a weakly acid acrylic resin (Bio-Rex 70) column (11×2.5 cm) slowly. The column was eluted with 5% and 50% acetic acid solution, respectively. [141$^1$, D-Tyr$^2$, Val$^4$, desGly$^9$]AVP was collected from 50% acetic acid solution fractions (860 mg).

[Pmp$^1$, D-Try$^2$, Val$^4$, desGly$^9$]AVP (25 μmol) in 4 ml of phosphate buffer is reacted with 2.6 ml of iodide solution and 2.6 ml of chloramine T solution at room temperature for 1 hour. Working up the mixture as described above gives [Pmp$^1$, D-Tyr$^2$(I), Val$^4$, desGly$^9$]AVP.

EXAMPLE 4

Pmp(Bzl)-D-Tyr(Br-Z)-Phe-Val-Asn-Cys(OMe-Bzl)-Pro-Arg(Tos)-Resin (4.2 g, 1.5 mM) from above, in 4.5 ml distilled anisole, was reacted with anhydrous hydrogen fluoride (40 ml) at 0° for one hour. After evaporation in vacuo to dryness, the residue was treated with anhydrous ether and filtered off to give 1.33 g crude peptide. The completion of removal of the Bzl group from the Pmp moiety was carried out using the sodium in liquid ammonia reaction as described above. The resulting unprotected octapeptide was cyclized using 0.01M potassium ferricyanide solution at pH 7-7.5 until color persisted for 30 minutes again as described above in the preparation of the amide.

[Pmp$^1$, D-Tyr$^2$, Val$^4$, desGly(NH$_2$)$^9$]AVP (600 mg) was collected after acidifying the oxidation solution with acetic acid to pH 4.5 and passing the reaction mixture over a Bio-Rex-70 column with 1 l. of 5% acetic acid as eluent.

[Pmp$^1$, D-Tyr$^2$, Val$^4$, desGly(NH$_2$)$^9$]AVP (18 μmol) in 3 ml of phosphate buffer is reacted with 2.1 ml of iodide solution and 2.1 ml of oxidizing solution at room temperature for 1 hour. Working up as described gives [Pmp$^1$, D-Tyr(I)$^2$, Val$^4$, desGly(NH$_2$)$^9$]AVP.

What is claimed is:

1. A polypeptide of the formula:

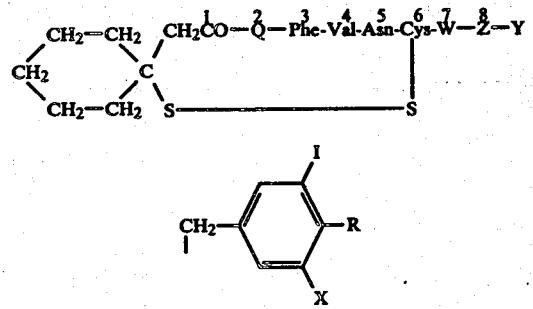

in which:
  Q is D- or L-NH—CH—;
  Y is NH$_2$, OH, Gly or Gly(NH$_2$);
  W is Pro;
  Z is D- or L-Arg;
  X is hydrogen or, when R is OH, I; and
  R is —OH or —O-alk of 1-2 carbons; or a pharmaceutically acceptable salt thereof.

2. The polypeptide of claim 1 in which Y is NH$_2$.

3. The polypeptide of claim 1 in which Y is Gly(NH$_2$).

4. The polypeptide of claim 1 in which X is H, R is OH, Z is L-Arg and Y is Gly(NH$_2$) which is [Pmp$^1$, D- or L-Tyr(I)$^2$, Val$^4$]AVP.

5. The polypeptide of claim 1 in which X is H.

6. The polypeptide of claim 1 in which Q is D-Tyr(I), Y is NH$_2$ and Z is L-Arg which is [Pmp$^1$, D-Tyr(I)$^2$, Val$^4$, desGly$^9$]AVP.

7. The polypeptide of claim 1 in which Q is D-Tyr(I), Y is Gly(NH$_2$) and Z is L-Arg which is [Pmp$^1$, D-Tyr(I)$^2$, Val$^4$]AVP.

8. A pharmaceutical composition having vasopressin antagonist activity comprising a nontoxic, effective therefor quantity of a polypeptide of claim 1 combined with a pharmaceutical carrier.

* * * * *